US008689801B2

(12) United States Patent
Ritchey et al.

(10) Patent No.: US 8,689,801 B2
(45) Date of Patent: Apr. 8, 2014

(54) TARGETING ORTHOPAEDIC DEVICE LANDMARKS

(75) Inventors: Nicholas S. Ritchey, Collierville, TN (US); Gene Edward Austin, Memphis, TN (US); Charles C. Heotis, Germantown, TN (US); Stefan R. Kirsch, Radolfzell (DE)

(73) Assignees: Smith & Nephew, Inc., Memphis, TN (US); Northern Digital, Inc., Waterloo (CA)

( * ) Notice: Subject to any disclaimer, the term of this patent is extended or adjusted under 35 U.S.C. 154(b) by 0 days.

(21) Appl. No.: 13/500,420

(22) PCT Filed: Oct. 6, 2010

(86) PCT No.: PCT/US2010/051678
§ 371 (c)(1),
(2), (4) Date: May 14, 2012

(87) PCT Pub. No.: WO2011/044273
PCT Pub. Date: Apr. 14, 2011

(65) Prior Publication Data
US 2012/0226094 A1    Sep. 6, 2012

Related U.S. Application Data

(60) Provisional application No. 61/249,245, filed on Oct. 6, 2009.

(51) Int. Cl.
*A61B 19/00*    (2006.01)
(52) U.S. Cl.
USPC ............................... 128/899; 606/62; 606/96
(58) Field of Classification Search
USPC ............... 128/899; 606/96–98; 600/407, 409, 600/424–427, 431
See application file for complete search history.

(56) References Cited

U.S. PATENT DOCUMENTS

| | | | | |
|---|---|---|---|---|
| 6,201,387 | B1 * | 3/2001 | Govari | 324/207.17 |
| 7,301,332 | B2 * | 11/2007 | Govari et al. | 324/207.21 |
| 2003/0066538 | A1 * | 4/2003 | Martinelli et al. | 128/899 |
| 2004/0011365 | A1 * | 1/2004 | Govari et al. | 128/899 |
| 2005/0070916 | A1 | 3/2005 | Hollstien et al. | |
| 2005/0075562 | A1 | 4/2005 | Szakelyhidi et al. | |
| 2005/0080335 | A1 | 4/2005 | Simon et al. | |
| 2005/0080427 | A1 | 4/2005 | Govari et al. | |
| 2006/0064149 | A1 * | 3/2006 | Belacazar et al. | 607/122 |

OTHER PUBLICATIONS

International Preliminary Report on Patentability for International Application No. PCT/US2010/051678, mailed Apr. 11, 2012, 5 pages.
Authorized Officer Kwon, Jang Seob; International Search Report/Written Opinion in PCT/US2010/051678, mailed Apr. 14, 2011, 8 pages.

* cited by examiner

*Primary Examiner* — Charles A Marmor, II
*Assistant Examiner* — Carrie R Dorna
(74) *Attorney, Agent, or Firm* — Fish & Richardson P.C.

(57) ABSTRACT

Targeting sensors for use in targeting landmarks of orthopaedic devices. The sensors include a non-cylindrical mounting platform such as a printed circuit board and at least two mounted or printed sensor coils to provide a low profile sensor assembly which can be placed in a predetermined position and orientation on or in an orthopaedic device. The platform has a non-circular cross-section having an aspect ratio of greater than about 1.5:1. The non-circular cross-section of the platform enables the sensor to be placed in a known fixed position within the implant. The sensor coils may be partially or fully embedded in the platform.

12 Claims, 7 Drawing Sheets

TARGETING ORTHOPAEDIC DEVICE LANDMARKS

CROSS-REFERENCE TO RELATED APPLICATION

This application claims priority to and the full benefit of U.S. Provisional Application Ser. No. 61/249,245, filed Oct. 6, 2009 and titled "LOW PROFILE INDUCTIVE ELECTROMAGNETIC SENSORS FOR TARGETING ORTHOPEDIC IMPLANTS," the entire contents of which are incorporated herein by reference.

TECHNICAL FIELD

This disclosure relates to targeting orthopaedic device landmarks.

BACKGROUND

Orthopaedic devices are used in many situations to stabilize and/or support bones and other tissues, such as fractured bones and bone fragments. During attachment of an orthopaedic device, it is sometimes necessary or beneficial to target one or more landmarks of the orthopaedic device. For example, obscured landmarks, such as fixation holes of an implanted orthopaedic device can be located using jigs and/or x-ray imaging. Once located, a tool and or a fastener can be engaged with the landmark. Additionally, visible landmarks can also be targeted to ensure proper or desired alignment of a tool or fastener with a landmark of the orthopaedic device. For example, a desired angle of insertion of a tool or a fastener relative to a landmark of the orthopaedic device can be achieved using a mechanical jig.

Alternatively, landmarks of orthopaedic devices can be targeted using electromagnetic spatial measurement systems, which determine the location of orthopaedic devices that are associated with inductive electromagnetic sensors in the form of sensor coils. When the orthopaedic device is placed within a magnetic field, voltage or current is induced in the sensor coils, which can be used by a measurement system to determine a position of the orthopaedic device. As the magnetic fields are of a low strength and can safely pass through human tissue, position measurement of the orthopaedic device is possible without line-of-sight constraints of optical spatial measurement systems.

In mechanics, degrees-of-freedom (DOF) are the set of independent displacements and/or rotations that specify a displaced location and rotational orientation of an object. For example, a particle that moves in three dimensional space has three translational displacement components and therefore three degrees-of-freedom (3 DOF). Translation is the ability to move without rotating, while rotation is angular motion about some axis. In contrast to a particle, a rigid body would have a maximum 6 DOF including three rotations and three translations. Specifically, in the case of a rigid body with d dimensions, the body has $d(d+1)/2$ degrees of freedom (d translations and $d(d-1)/2$ rotations). Therefore, a rigid body with three dimensions (X, Y and Z), has a maximum 6 DOF. As used herein, a position of an object includes translational locations and rotational orientations that define the position of the object in three dimensional space.

Figure 1:
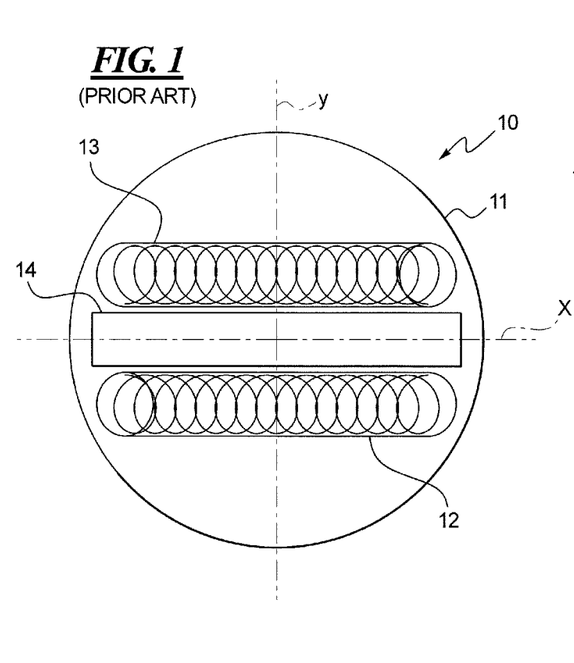
FIG. 1 is an end view of a prior art inductive electromagnetic sensor.
Figure 2:
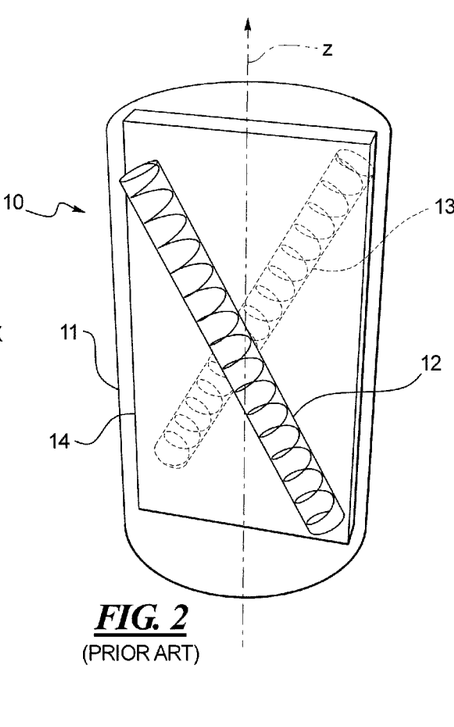
FIG. 2 is a top plan view of the sensor shown in FIG. 1.

Currently available electromagnetic sensors may be embedded in or attached to an object such as a surgical instrument or orthopaedic implant to allow the position of the object to be displayed in the correct anatomical context in real-time. Referring to FIGS. 1-2, electromagnetic sensors 10 may be arranged in a cylindrical body or rod 11. The sensors 10 comprise two coils 12, 13 placed on top of each other in a crosswise configuration with a printed circuit board (PCB) 14 disposed between the coils 12, 13 to protect the coils 12, 13 from breakage. If only a 5DOF sensor is needed for a spatial tracking application, the arrangement illustrated in FIGS. 1-2 is acceptable because the rotation about the diameter of the cylinder or the z-axis (FIG. 2) may be disregarded. However, the arrangement of FIGS. 1 and 2 requires the structure that houses the sensor 10 to be at least twice as thick as the diameter of the coils 12, 13 to accommodate the crossing configuration of the coils 12, 13 and the body or rod 11. Further, because 6 DOF sensors are required or beneficial for some targeting applications, e.g., targeting a distal end of an orthopaedic implant, such as an intramedullary nail, the circular cross-sectional shape of the sensor housing 11 (FIG. 1) makes it difficult to consistently place the sensor 10 in a predetermined orientation in the implant because the cylinder 11 tends to rotate about its z-axis (FIG. 2) during assembly and, as a result, the predetermined orientation of the coordinates may change during assembly.

SUMMARY

Targeting sensors for use in targeting landmarks of orthopaedic devices are disclosed. The inductive electromagnetic sensors can be embedded in the orthopaedic devices, disposed on the orthopaedic devices, or used in association with the orthopaedic devices, such as in or on a probe that is removably associated with an orthopaedic device. The sensors can include a mounting platform such as a PCB and at least two mounted or printed sensor coils.

In one general aspect, an orthopaedic device includes an inductive electromagnetic sensor having a non-cylindrical mounting platform and at least two sensor coils. The sensor coils are connected to the platform in a generally co-planar fashion and at an angle with respect to each other, the sensor coils not overlying each other.

Implementations can include one or more of the following features. For example, the platform has an aspect ratio of greater than about 1.5:1. The platform has an aspect ratio ranging from about 1.5:1 to about 5:1, ranging from about 2:1 to about 3:1, or of about 2.5:1. The platform has a height and a width, the height ranging from about 0.2 mm to about 1 mm, the height being smaller than the width. The width of the platform is less than about 3 mm. The width of the platform ranges from about 1 mm to about 3 mm. The at least two coils of the sensor form an angle θ with respect to each other ranging from about 15° to about 175°, or from about 15° to about 90°. The coils are at least partially embedded in the platform. The platform is a printed circuit board comprising a polyamide polymer. The printed circuit board has a generally rectangular cross-section with an aspect ratio greater than about 1.5:1. The printed circuit board further comprises a plurality of conductive traces and solder joints. The orthopaedic device is an intramedullary nail and the sensor is disposed in a distal portion of the intramedullary nail. The orthopaedic device further includes an elongated body having an outer surface with at least one structure for accommodating the inductive electromagnetic sensor. The orthopaedic device is a probe configured for removable engagement with an orthopaedic stabilizing structure.

In another general aspect, an orthopaedic device includes an elongated body having an outer surface with at least one structure for accommodating an inductive electromagnetic sensor. The inductive electromagnetic sensor includes a non-cylindrical mounting platform engaged with the at least one structure and at least two sensor coils mounted on the platform, the sensor coils being connected to the platform in a generally co-planar fashion and at an angle θ with respect to each other, the sensor coils not overlying each other.

Implementations can include one or more of the following features. For example, the platform has an aspect ratio ranging from about 1.5:1 to about 5:1, from about 2:1 to about 3:1, or of about 2.5:1. The platform has a height and a width, the height ranging from about 0.2 mm to about 1 mm, the height being smaller than the width, and the width ranging from about 1 mm to about 3 mm. The width of the platform is less than about 3 mm. The at least two coils of the sensor form an angle θ with respect to each other ranging from about 15° to about 175°, or from about 15° to about 90°. The coils are at least partially embedded in the platform. The platform is a printed circuit board comprising a polyamide polymer, the printed circuit board having a rectangular cross-section with an aspect ratio greater than about 1.5:1. The printed circuit board further comprises a plurality of conductive traces and solder joints.

In another general aspect, a system for identifying a landmark includes a field generator for generating a magnetic field, an orthopaedic device located within the magnetic field, the orthopaedic device having at least one landmark, at least one sensor, the at least one sensor comprising a non-cylindrical mounting platform and at least two sensor coils mounted on the platform, the sensor coils being connected to the platform in a generally co-planar fashion and at an angle θ with respect to each other, the sensor coils not overlying each other, the sensor being spaced apart from the at least one landmark by a set distance, a landmark identifier, and a processor for processing sensor data from the at least one sensor and using the set distance to determine the position of the landmark identifier relative to the at least one landmark.

Implementations can include one or more of the following features. For example, the landmark identifier includes a second sensor. The landmark is selected from the group consisting of a structure, a void, a boss, a channel, a detent, a flange, a groove, a member, a partition, a step, an aperture, a bore, a cavity, a dimple, a duct, a gap, a notch, an orifice, a passage, a slit, a hole, or a slot. The orthopaedic device is an intramedullary nail. The orthopaedic device has an outer surface having a recess, an inner surface forming a cannulation, and a wall there between, and the recess and first sensor being disposed within the wall. The orthopaedic device further comprises a cover disposed over the recess and the first sensor. The landmark identifier further includes a drill sleeve. The landmark identifier further includes a serrated tip. The processor provides feedback information to a user. The landmark identifier includes the field generator. The at least one sensor is attached to a probe that is removable from the orthopaedic device. The landmark identifier further includes a sleeve, the sleeve having a longitudinal axis at a known position relative to the magnetic field. The longitudinal axis is generally coaxial with an axis of a reference coordinate system associated with the magnetic field.

In another general aspect, a method for identifying a landmark includes providing an orthopaedic device and a first sensor disposed at a known location relative to the orthopaedic device, the orthopaedic device having a proximal end portion, a distal end portion and at least one landmark disposed on the distal end portion, the first sensor comprising a non-cylindrical mounting platform and at least two sensor coils mounted on the platform, the sensor coils being connected to the platform in a generally co-planar fashion and at an angle θ with respect to each other, the sensor coils not overlying each other, attaching the orthopaedic device to one or more bones of a patient, targeting a landmark using a landmark identifier and an output of the first sensor, and engaging at least one of a tool and a fastener with the landmark using the landmark identifier.

It should be understood that the drawings are not necessarily to scale and that the disclosed implementations are sometimes illustrated diagrammatically and in partial views. In certain instances, details which are not necessary for an understanding of the disclosure or which render other details difficult to perceive may have been omitted. It should be understood that this disclosure is not limited to the particular implementations illustrated herein.

DETAILED DESCRIPTION

Figure 3:
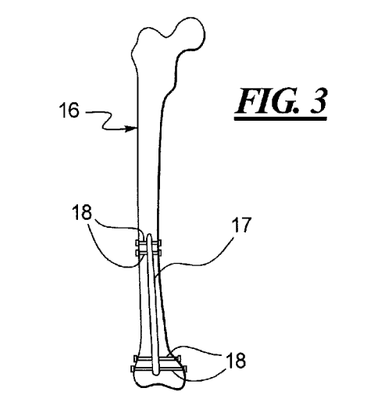
FIG. 3 is a schematic illustration of a femur with an intramedullary nail implanted therein.
Figure 4:
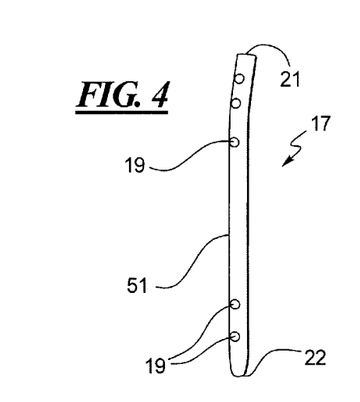
FIG. 4 is a perspective view of an intramedullary nail that may be equipped with one or more targeting sensor.
Figure 8:
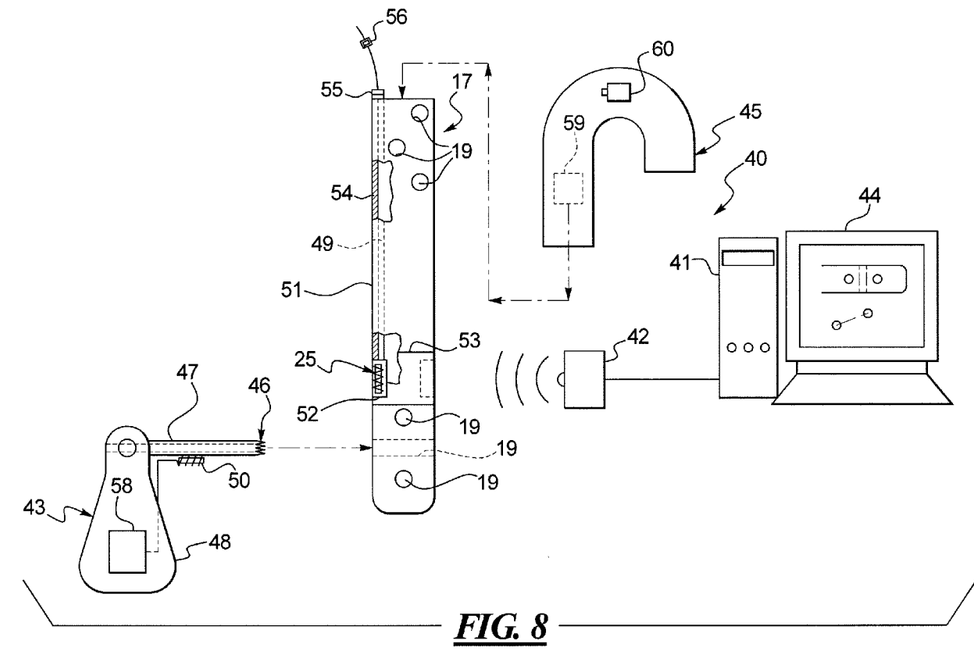
FIG. 8 is a schematic illustration of a system for targeting landmarks of an orthopaedic device.

FIG. 3 illustrates a femur 16 with an intramedullary nail 17 disposed in the femur 16 and held in place by a plurality of pins or screws 18. A perspective view of an intramedullary nail 17 is provided in FIG. 4. The pins or screws 18 are received in the transfixion holes 19. The nail 17 includes proximal and distal ends 21, 22 respectively. To provide the surgeon with information regarding the position of the transfixion holes 19 or other landmarks, one or more inductive electromagnetic sensors 25 (FIG. 5) may be installed on or in the intramedullary nail 17, with at least one sensor 25 disposed towards the distal end 22 of the intramedullary nail 17 as illustrated in FIG. 8. The sensor 25 disposed towards the distal end 22 of the nail 17 may be a 6 DOF sensor.

Figure 5:
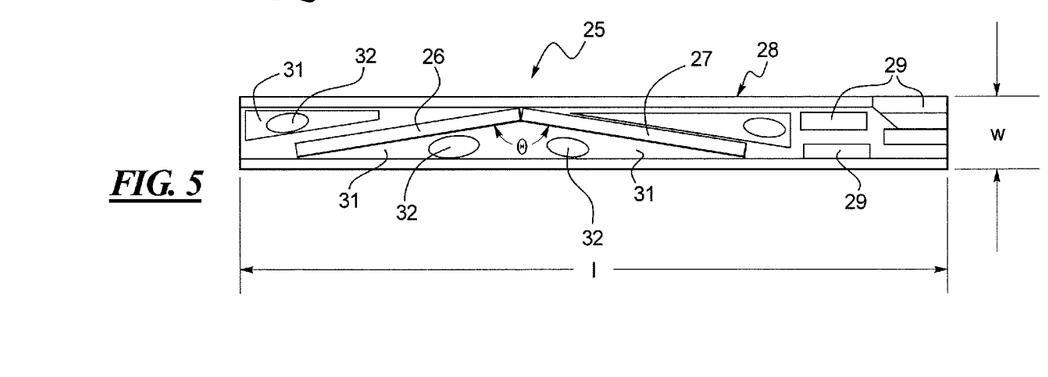
FIG. 5 is a top plan view of an inductive electromagnetic sensor.

Turning to FIG. 5, the sensor 25 includes two coils 26, 27 that are mounted on or printed on a platform 28 in a coplanar fashion. The platform 28 also supports electronic components 29 and conductive traces 31 for accommodating solder joints 32. The platform 28 has a width w, a length l and a thickness or height h (FIG. 6).

Figure 6:
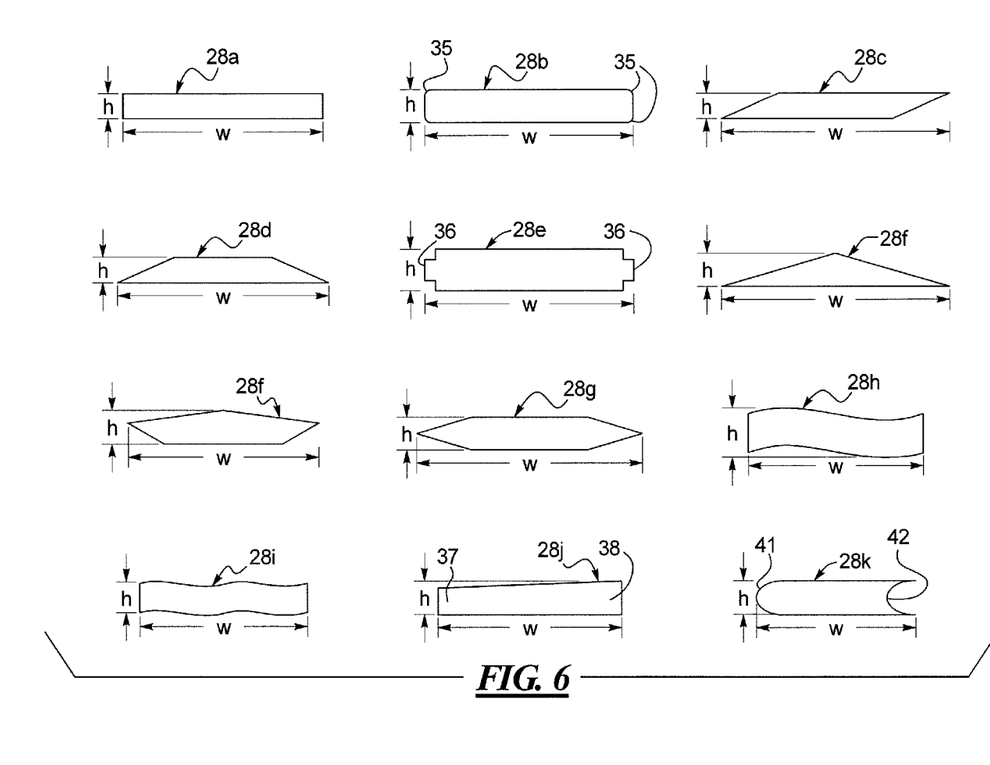
FIG. 6 illustrates end views illustrating non-circular or non-cylindrical cross-sections of 12 different platforms for use in an inductive electromagnetic sensor.

Specifically, turning to FIG. 6, twelve different platforms 28a-28k with different cross-sectional profiles are shown. Each platform 28a-28k has a width w and a thickness or height h. The platform 28a features a rectangular cross-sectional profile; the platform 28b features a rectangular cross-sectional profile with rounded edges 35; the platform 28c features a parallelogram-shaped cross-sectional profile; platform 28*d* features a trapezoidal-shaped cross-sectional profile; the platform 28*e* features a rectangular cross-sectional profile with lateral tongues 36 that could be received in complementary slots disposed in an orthopaedic device or a probe (not shown); the platform 28*f* features a triangular-shaped cross-sectional profile; the platform 28*f* features an irregular pentagonal-shaped cross-sectional profile; the platform 28*g* features a hexagonal-shaped cross-sectional profile; the platforms 28*h* and 28*i* feature curved cross-sectional profiles; the platform 28*j* features an irregular quadrilateral-shaped cross-sectional profile with one side 37 being shorter than the other side 38; and the platform 28*k* features one rounded or convex side 41 and one concave side 42. Generally, almost any non-circular cross-sectional profile can be utilized for the platform 28.

Figure 7:
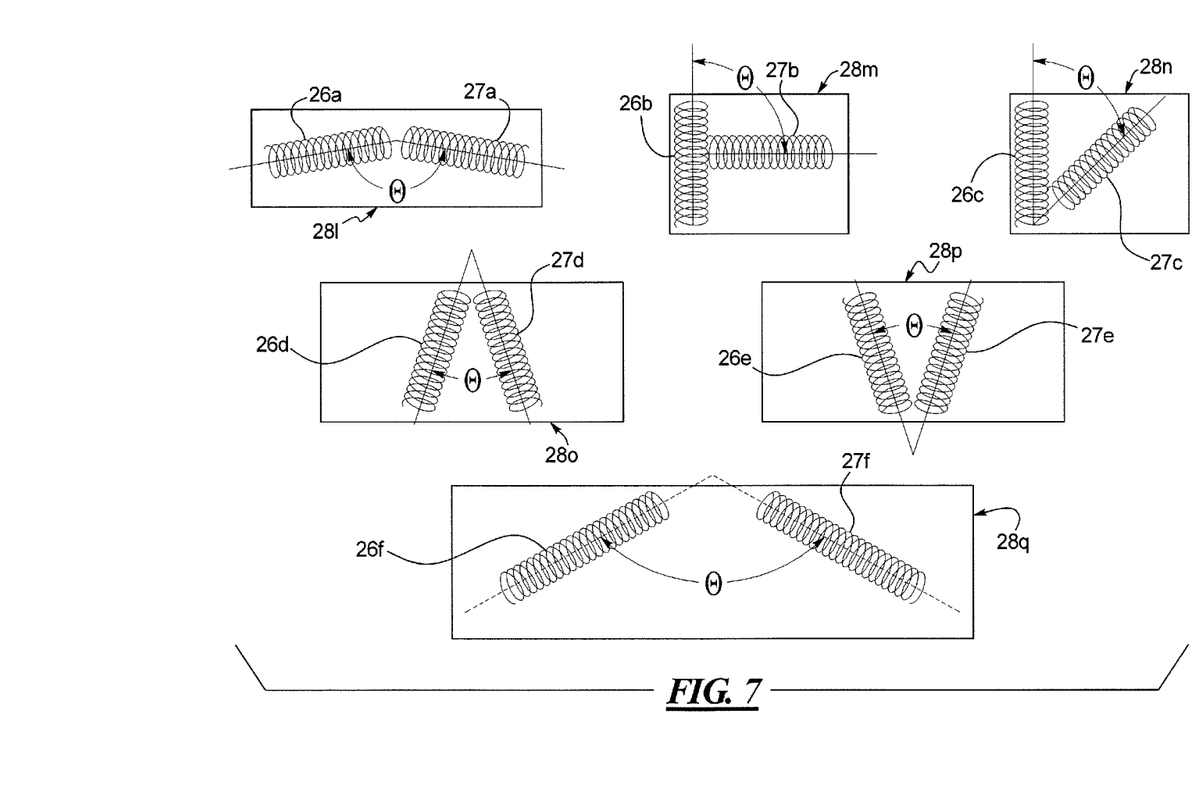
FIG. 7 illustrates top plan views of coil arrangements for an electromagnetic sensor.

In FIG. 5, the coils 26, 27 are disposed at an angle θ of about 160° with respect to each other. The angle θ between the coils 26, 27 can vary greatly as illustrated in FIG. 7. Specifically, the coils 26*a*, 27*a* that are disposed on the platform 28*l* are disposed at an angle θ of about 165° with respect to each other; the coils 26*b*, 27*b* that are disposed on the platform 28*m* are disposed at an angle θ of about 90° with respect to each other; the coils 26*c*, 27*c* that are disposed on the platform 28*n* are disposed at an angle θ of about 45° with respect to each other; the coils 26, 27*a* that are disposed on the platform 28*o* are disposed at an angle θ of about 60° with respect to each other; the coils 26*e*, 27*e* that are disposed on the platform 28*p* are disposed at an angle θ of about 110° with respect to each other; and the coils 26*f*, 27*f* that are disposed on the platform 28*q* are disposed at an angle θ of about 135° with respect to each other.

The inductive electromagnetic sensors 25 may be embedded in an orthopaedic device, such as an intramedullary nail 17 or used in association with a probe or other structure attached to the orthopaedic device. For example, the probe can be removably engaged with an intramedullary nail, a bone plate, or other orthopaedic stabilizing structure. The sensors 25 include a non-cylindrical mounting platform 28-28*k* that may be in the form of a PCB with a non-circular or non-cylindrical shape and size and at least two mounted or printed sensor coils 26-26*f*, 27-27*f* to provide a low profile sensor 25 which can be consistently placed in the pre-determined position in an orthopaedic device 17 during the implant manufacture or assembly or that can be disposed in a probe that is removably engageable with an orthopaedic device 17, such as an implant, external fixation device, or other stabilizing structure. The platforms 28-28*q* preferably have an aspect ratio (i.e., a ratio of the width w to the height h) of greater than about 1.5:1, more preferably greater than 2.0:1. In some implementations, the sensor 25 has an aspect ratio of about 2.5:1. In general, the height of the sensors 25 may fall in the range of about 0.2 mm to about 1 mm and the diameters of the coils 26-26*f*, 27-27*f* may be the predominant factor in determining the height of the sensors 25. The width of the sensors 25 may fall in the range of about 1 mm to about 3 mm. Both the width w and/or length l of the platform 28-28*q* can be dimensioned to accommodate the angle θ formed between the coils 26-26*f*, 27-27*f*. Specifically, the width w increases as θ approaches 90°, while the length l decreases as θ approaches 90°. As θ approaches 180° or 0°, the width w of the platforms 28-28*a* is reduced and the length l is increased. In general, the at least two coils 26-26*f*, 27-27*f* form an angle θ ranging from about 15° to about 175°. Furthermore, to conserve space, the coils 26-26*f*, 27-27*f* are arranged in a co-planar fashion on the platform 28-28*q*, not on top one other. The coils 26-26*f*, 27-27*f* can be partially or completely embedded in the mounting platform 28-28*q*. This shaping and dimensioning of the platform 28-28*q* and the coils 26-26*f*, 27-27*f* arrangement provides low profile sensors 25 that can be consistently placed in or on an orthopaedic implant 17 with known positions. The platforms 28-28*q* are made of a non-conductive, non-magnetic material.

The inductive electromagnetic sensor assembly of FIG. 5 includes a platform 28 in the form of a printed circuit board having a rectangular cross-section having a width w of about 2.5 mm and a height or thickness h of about 1 mm. Additional conductive traces 31 are printed on the platform or board 28 to allow solder joints 32 to be arranged to conserve space. The platform or board 28 may include a polyamide polymer. The two sensor coils 26, 27 are partially embedded in the platform or board 28, are generally co-planar and form an angle θ ranging from about 140° to about 170°.

FIG. 8 illustrates one disclosed system 40 for identifying landmarks, such as holes 19 in an intramedullary nail 17. The system 40 may include a processor 41, a magnetic field generator 42, a landmark identifier 43, and an orthopedic device, i.e., the intramedullary nail 17 equipped with one or more sensors 25. In some implementations, the system 40 may also include a monitor 44 electrically coupled to the processor 41. The system 40 may also include an insertion handle 45 removably attached to the intramedullary nail 17. The processor 41 is depicted as a desktop computer in FIG. 8, but other types of computing devices may be used. As examples, the processor 41 may be a desktop computer, a laptop computer, a personal data assistant (PDA), a mobile handheld device, or a dedicated device. The magnetic field generator 42 can be a device available from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. However, other generators may be used; for example, the field generator 42 may provide a pulsed direct current electromagnetic field or an alternating current electromagnetic field. In some implementations, the system 40 may also include a control unit (not shown) coupled to the magnetic field generator 42. The control unit may control the field generator 42, receive signals from small mobile inductive sensors, and communicate with the processor 41, either by wire or wirelessly. In some embodiments, the control unit may be implemented in the processor 41 either through hardware or software.

The magnetic field generator 42 includes suitably arranged electromagnetic inductive coils that provide a spatial magnetic reference coordinate system (i.e., X, Y, and Z axes). The position of the small mobile inductive sensor 25 associated with the intramedullary nail 17 is determined from outputs of the sensor 25 based on the source field produced by magnetic field generator 42.

The magnetic field generator 42 may generate a sequence, or set, of different spatial magnetic field shapes, or distributions, each of which is sensed by the inductive sensor 25. For example, six different magnetic field shapes may be generated in a repeated sequence. Each magnetic field of the sequence causes the inductive sensor 25 to produce an output signal (possibly including a null signal) such that the sensor 25 generates a sequence of output signals based on the sequence of magnetic fields. Processing of the sequence of output signals enables determination of the position of the sensor 25 relative to the spatial reference magnetic coordinate system provided by the electromagnetic field generator 42. Thus, the position of the intramedullary nail 17 and various landmarks of the intramedullary nail 17 associated with the sensor 25 relative the spatial reference magnetic coordinate system can be determined based on a known position of the sensor 25 relative to the intramedullary nail 17. The processor 41 or the control unit uses the spatial reference magnetic coordinate system and the sensor outputs to create a transformation matrix comprising position information.

The landmark identifier 43 is used to target a landmark, such as a transfixion hole 19, of the intramedullary nail 17. The landmark identifier 43 may include one or more small mobile inductive sensors 50, which may have a similar or identical construction and/or operation to that of the sensor 25. The landmark identifier 43 may be any number of devices; for example, the landmark identifier 43 may be a drill guide, a drill sleeve, a drill, a drill nose, a drill barrel, a drill chuck, or a fixation element. As shown in FIG. 8, the landmark identifier 43 is a drill sleeve having a serrated tip 46, a tube 47, and a handle 48. The tube 47 also may be referred to as a bushing, cylinder, guide, or drilling/screw placement guide. In some implementations, the landmark identifier 43 includes a drill sleeve having a longitudinal axis along which a drill bit is received. The longitudinal axis is arranged in a known position relative to an axis of the reference coordinate system of the electromagnetic field generator. For example, the longitudinal axis can be generally parallel to or coaxial with an axis of the reference coordinate system of the electromagnetic field generator.

The second sensor 50 is arranged in a known position relative to an axis of the tube 47, which may receive a drill bit or other tool. The know position of the sensor 50 relative to the tube 47 allows the position of the tube 47 in space to be determined for six dimensions (three translational and three rotational) relative to the magnetic field generator 42 or another sensor in the system, such as the sensor 25 associated with the intramedullary nail 17. In some implementations, the processor 41 may need to be calibrated to adjust for the position of the second sensor 50 relative to the tube 47 or another feature of the landmark identifier 43. In some implementations, the landmark identifier 43 may include the field generator 42, such as incorporated within the handle 48, and the sensor 50 may be omitted.

In addition to the intramedullary nail 17, other orthopaedic devices can include the sensor 25 for targeting landmarks of the orthopaedic devices. For example, the orthopaedic device may be a bone plate, a hip prosthetic, a knee prosthetic, or other joint prosthesis, or an external fixation device, or a component of any of these.

Figure 9:
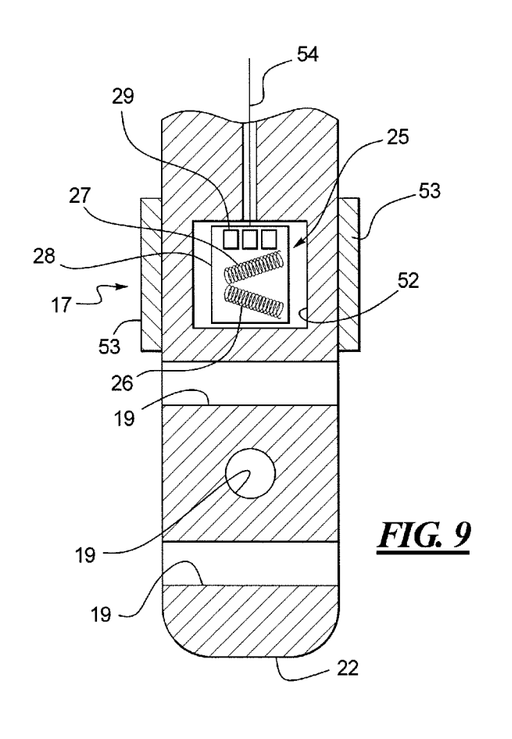
FIG. 9 is an enlarged partial view of the distal end of the orthopaedic device of FIG. 8 illustrating a different cover.

As shown in FIG. 9, the sensor 25 is disposed in a known position relative to one or more landmarks on the intramedullary nail 17. As mentioned above, the landmark may any readily identifiable structure of the intramedullary nail 17 or other orthopaedic device, such as a the transfixion holes 19 or any one or more of a void, a boss, a channel, a detent, a flange, a groove, a member, a partition, a step, an aperture, a bore, a cavity, a dimple, a duct, a gap, a notch, an orifice, a passage, a slit, a slot or combinations thereof. The offset of the sensor 25 from the landmarks 19 allows the position of the landmarks 19 to be located in space in six dimensions (three translational and three rotational) relative to the magnetic field generator 42 and/or another sensor in the system, such as the second sensor 50. In some implementations, the processor 41 may need to be calibrated to adjust for the offset distance of the sensor 25 from one or more landmarks of interest.

The sensor 25 and the second sensor 50 are coupled to the processor 41 by wire, wirelessly, or by a combination of wired and wireless coupling. The sensor 25 and the second sensor 50 are 6 DOF sensors configured to output signals that allow the position of each sensor 25, 50 for three translational axes, generally called X, Y and Z and for three angular orientations, generally called pitch, yaw and roll. By determining the positions of the sensors in these reference frames, the landmark identifier 43 may be positioned relative to the landmarks 19 on the intramedullary nail 17. For example, the signals received from the sensors 25, 50 allows for a surgeon to plan the surgical path for fixation and properly align a drill or other tool with an obscured fixation hole 19. In some implementations, the sensors 25, 50 are 6 DOF sensors from: Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Other sensors may be used as will be apparent to those skilled in the art.

The sensor 25 may be attached to, embedded in, or otherwise coupled to the intramedullary nail 17. For example, the sensor 25 may be attached to an outer surface 51 of the intramedullary nail 17. In some implementations, the intramedullary nail 17 may also include a pocket or recess 52 (best seen in FIG. 9). The recess 52 is located in a wall of the intramedullary nail 17. Thus, in some implementations, the sensor 25 is intended to be attached to the intramedullary nail 17 and installed in a patient for the service life of the intramedullary nail 17. Additionally, the intramedullary nail 17 may include a cover 53 to cover the pocket or recess 52. As shown in FIG. 8, the cover 53 may be substantially flush with the external surface 51 of the intramedullary nail 17 or, as shown in FIG. 9, the cover 53 may be wrapped around the intramedullary nail 17. The sensor 25 may be tethered to leads 54 for communication and power. The leads 54 and sensor 25 may be fixed to the intramedullary nail 17, such as by a potting material and/or an adhesive. The lead 54 may be disposed in a longitudinal slot or groove 49 in the outer surface 51 of the intramedullary nail 17. The lead 54 may be used to connect the sensor 25 to the processor 41 or the control unit. The lead 54 may be made from biocompatible wire, such as DFT® wire available from Fort Wayne Metals Research Products Corp., 9609 Indianapolis Road, Fort Wayne, Ind. 46809. A first connector 55 may be used to connect the lead 54 to another device, such as the processor 41, the control unit, or the insertion handle 45. In some implementations, a second connector 56 may also be used to connect the lead 54 to the processor 41.

As mentioned above, the sensor 25 may be secured in the recess 52 using a high stiffness adhesive or polymer, such as an epoxy resin material, a polyurethane material, a polymethyl methacrylate material, a polyetheretherketone material, a UV curable adhesive material, a silicone material, or a medical grade cyanoacrylate material. For example, EPO-TEK 301 available from Epoxy Technology, 14 Fortune Drive, Billerica, Mass. 01821 may be used. The lead 54 may be fixed in the groove 49 in other suitable manners that do not adversely affect the performance of the electrical components of the sensor 25 and that do not adversely affect the performance of the intramedullary nail 17. After fixation of the sensor 25, the cover 53 may be placed on the intramedullary nail 17 and secured in-place. For example, the cover 53 may be laser welded to the implant.

In some implementations, the sensor 25 can be removably attached to the intramedullary nail 17. For example, the sensor 25 can be installed in the groove 49 for use during implantation and fixation of the intramedullary nail 17 and the sensor 25 can be removed from the intramedullary nail 17 before completion of the surgery, such as by pulling the sensor 25 and associated lead wires 54 out of the groove. Similarly, the sensor 25 can be disposed in a probe that is removably engageable with the intramedullary nail 17 such that the sensor 25 can be used for targeting landmarks of the intramedullary nail 17 and then can be removed from the intramedullary nail 17.

The monitor 44 may be configured to display the position of the landmark identifier 43 and/or a tool associated with the landmark identifier 43 relative to one or more landmarks of the intramedullary nail 17 or other orthopaedic device. The processor 41 may determine positional data and output a representation of the positional data through a user interface, which may graphically display the relative positions of the landmark identifier 43 and the intramedullary nail 17 on the monitor 44. The view displayed on the monitor 44 may be oriented relative to intramedullary nail 17 or other orthopaedic device so that a surgeon or other operator may visualize the current relative position of the landmark identifier 43 relative to the intramedullary nail 17 or other orthopaedic device. In some implementations, the surgeon or other operator may view the monitor 44 simultaneously with the surgical field.

The insertion handle 45 may be used for installation of the intramedullary nail 17 and also may be used to route the leads 54 from the sensor 25. For example, the insertion handle 45 may route both communication and power leads between the implant 17 and the processor 41. In such implementations, removal of the insertion handle 45 from the intramedullary nail 17 also effects removal of at least a portion of the leads 54 or a connector, such as the second connector 55.

As shown in FIG. 8, the landmark identifier 43 and the insertion handle 45 each include a communications module 58, 59 for wirelessly transmitting data from the sensors 25, 50 to the processor 41. However, other types of communication, such as wired communication, may be used. In some implementations, the second connector 56 connects the communications module 59 to the sensor 25. Alternatively, the intramedullary nail 17 and the insertion handle 45 may have mating electrical contacts that form a connection when the components are assembled such that the sensor 25 is coupled to the communications module 59.

In some implementations, the intramedullary nail 17 may include a communications circuit and an antenna for wireless communication (not shown). Additionally, a power source for the sensor 25 and/or the communications module 59 may be disposed within the insertion handle 45. For example, a battery 60 may be housed within the insertion handle 45 for providing electrical power to the sensor 25, the transmission module 59 and/or other electronic components. Alternatively, the intramedullary nail 17 may include an inductive coil that is operable to inductively power the communications module 59 and communicate data from the sensor 25. The power source may be a single source mode or may be a dual mode AC/DC.

In use, the intramedullary nail 17 is implanted in a patient. For example, the intramedullary nail 17 is placed within an intramedullary canal of the patient's bone. Optionally, transfixion elements, such as screws or pins, may be used to temporarily or permanently (such as for the duration of use of the intramedullary nail 17) lock the proximal end of the intramedullary nail. An operator can use the landmark identifier 43 and the sensor 25 to identify landmarks of the intramedullary nail 17 with which the transfixion elements engage. For example, a surgeon uses the landmark identifier 43 to identify obscured transfixion holes 19, drills through the holes 19 for the correct placement of the transfixion elements 18, and installs the transfixion elements 18.

Figure 10:
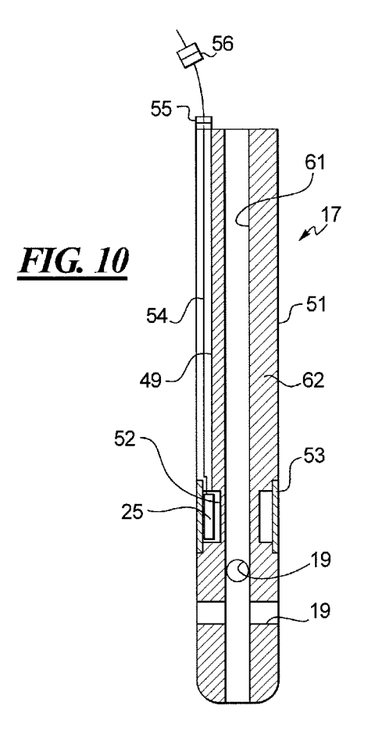
FIG. 10 is a sectional view of the orthopaedic implant of FIG. 8.

FIG. 10 further illustrates the intramedullary nail 17 shown in FIG. 8, which may include the sensor 25, the longitudinal groove 49, the pocket or recess 52 for accommodating the sensor 25, and the cover 53 generally flush with the outer surface 51 of the intramedullary nail 17. In some implementations, the cover 53 may be formed of gold or titanium foil and the implant 17 may include a cannulation or passageway 61. The intramedullary nail 17 includes the outer surface 51 with a wall 62 extending between the surface 51 and internal passageway 61.

Figure 11:
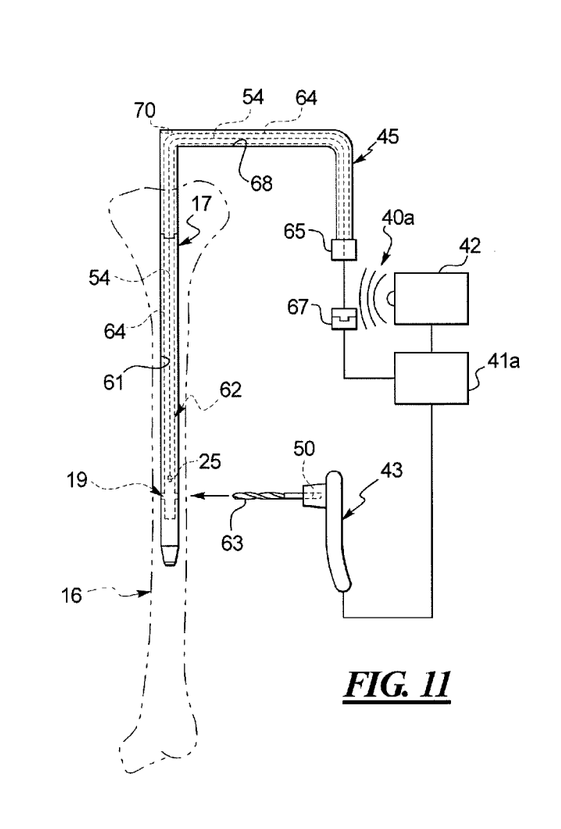
FIG. 11 is a schematic illustration of a system for targeting landmarks of an orthopaedic device.

Alternatively, where the cannulation or passageway 61 is included in the intramedullary nail 17 or other orthopaedic device, the sensor 25 can be disposed within the passageway or cannulation 61, such as when disposed on or in a probe. For example, as illustrated in FIG. 11 a system 40a for targeting landmarks of the intramedullary nail 17 implanted in a bone 16. The system 40a includes a control unit 41a, a field generator 42, a landmark identifier 43a, and a probe 62 disposed within the intramedullary nail 17. The control unit 41a may include the processor 41 described above in FIG. 8 or a similar device, or the processor 41 may be a separate unit. The intramedullary nail 17 includes one or more landmarks 19, such as transfixion holes, and is inserted into the bone 16 using the insertion handle 45 such that the landmarks 19 are obscured from view. The field generator 42 is connected to the control unit 41 a. In some implementations, the insertion handle 45 may include a third sensor 70.

The landmark identifier 43 may include a second sensor 50 and may guide a drill bit 63. The landmark identifier 43 may be attached to or include a drill for rotating the drill bit 63. The second sensor 50 may be coupled to the control unit 41a, either by wire or wirelessly. In some implementations, the field generator 42 may also be included in the landmark identifier 43 and the second sensor 50 can be omitted.

The probe 62 may include a wire or lead 54, a tape body 64, and a stop 65. The tape body 64 may be, for example, about 0.125 inch wide by about 0.060 inch thick 300 series stainless steel fish tape available from Ideal Industries, Inc. of Sycamore, Ill. However, those of ordinary skill in the art would understand that other materials and other sizes may be used. For example, any narrow band of polymer, composite material, or metal may be used as the tape body 64, or it may be beneficial to use a non-ferrous metal material. The tape body 64 may be coiled before placement into the IM nail 17. Coiling of the tape body 64 may cause it to have a natural curvature. The tape body 64 may have, in some implementations, a rectangular geometry that assists in orienting the tape body as it is placed into a cannulation 61 of the intramedullary nail 17. For example, an oval, square, or circular geometry also may be used. The wire 54 may be operatively coupled to the tape body 64 through the use of an adhesive or fastener. The tape body 64 may include graduations or detents to indicate a depth of the tape as it is inserted into the nail 17. The phone 62 may have a housing other than the tape body 64, such as a hollow tube, or other structure.

A first sensor 25 is coupled to the control unit 41a, either by wire or wirelessly. For example, the first sensor 25 may connected to the control unit 41a through the use of the wire 54 and a connector 67. In other embodiments, the connector 67 may be omitted or replaced with a communications module like the one shown at 59 in FIG. 8. The first sensor 25 may be coupled to a distal end of the tape 64, and the stop 65 may be coupled to a proximal end of the tape 64.

In some implementations, the probe 62 may include a sensor housing (not shown) to house the first sensor 25. The sensor housing may be attached to the tape 64 to secure the sensor 25 in a known position relative to the tape body 64. The sensor housing may be made of a non-ferrous material, such as a polymer, a composite, or a metal. The sensor housing may include an appropriate strain relief to shield the wire 54 and/or the sensor 25 from forces that could damage the wire 54 or the sensor 25. The sensor housing may be constructed and arranged such that it is large enough to hold the first sensor 25 but is small enough to fit within the cannulation 68 of the insertion handle 45 or within the cannulation 61 of the intramedullary nail 17. Further, the sensor housing may be constructed and arranged to be long enough to allow passage through intramedullary nail bends, intramedullary nail bow, and/or bends in relevant instrumentation. Geometries of the leading and trailing faces of the sensor housing may be designed such that the sensor housing does not catch or snag on the cannulation of the instrumentation or intramedullary nail 17.

The stop 65 may be used to control the insertion of the probe 62 within the cannulation 61 to effect placement of the sensor 25 at a known position relative to the intramedullary nail 17. For example, if the tape body 64 has a fixed length and the distance from the end of the insertion handle 45 to the landmark 19 is known, repeatable placement of the first sensor 25 relative to the landmark 19 may be achieved by abutting the stop 65 against the end of the insertion handle 45. The tape body 64 may have a sufficient length such that the sensor 25 is aligned with the landmark 19, adjacent the landmark 19, or offset from the landmark 19. In some implementations, the insertion handle 45 may be omitted, and a different tape body can be used that has a length selected such that the stop 65 engages a portion or end of the intramedullary nail 17. Similarly, the stop 65 may be separate from the probe 62 and can be removably engageable with the insertion handle 45 and/or the intramedullary nail 17 to limit insertion of the probe 62 into the cannulation 61.

Figure 12:
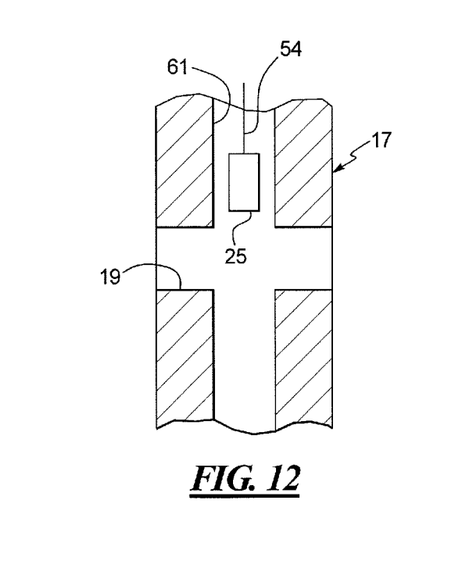
FIG. 12 is a partial cross-sectional view of the orthopaedic device of FIG. 11.

FIG. 12 illustrates a detailed view of the intramedullary nail 17, the sensor 25, the lead 54 and the landmark 19, with the tape body 64 and the sensor housing being omitted for the sake of clarity. As shown, the sensor 25 is positioned generally adjacent to the landmark 19 such that the sensor 25 does not interfere with insertion of the drill bit 63 and/or a transfixion element through the landmark 19.

In use, the intramedullary nail 17 is placed into the bone 16. The insertion handle 45 may be attached to the intramedullary nail 17. The probe 62 is fed through the cannulation 68 of the insertion handle 45 and into the cannulation 61 of the intramedullary nail 17 until the stop 65 engages the insertion handle 45 as illustrated in FIG. 11. The wire or lead 54 may be coupled to the control unit 41a, and the sensors 25, 50, and 70 may be calibrated using the control unit 41a. In some embodiments, the probe 62 may be removed after calibration. If so, the third sensor 70 and a transformation matrix may be used to identify the relative position of the second sensor 50 and the position of the landmark identifier 43. Optionally, the user may use transfixion elements, such as screws, to first lock the proximal end of the intramedullary nail. An operator uses the landmark identifier 43 and the first sensor 25 to identify the landmarks 19. For example, in the case of intramedullary nail fixation, a surgeon uses the landmark identifier 43 to identify the blind transfixion holes and drill through the holes for placement of a transfixion element.

While only certain implementations have been set forth, alternatives and modifications will be apparent from the above description to those skilled in the art. These and other alternatives are considered equivalents and within the spirit and scope of this disclosure and the appended claims.

The invention claimed is:

1. An orthopaedic device comprising:
   an inductive electromagnetic sensor comprising:
      a non-cylindrical mounting platform comprising a printed circuit board comprising a polyamide polymer, the printed circuit board having a generally planar surface and an aspect ratio of greater than about 1.5:1, the mounting platform having a height and a width, the height being smaller than the width, wherein the height ranges from about 0.2 mm to about 1 mm, and the width is less than about 3 mm; and
      at least two sensor coils mounted to the generally planar surface of the printed circuit board, each of the at least two sensor coils defining a central axis, the at least two sensor coils configured to provide data indicating a position in six degrees of freedom in response to receiving electromagnetic fields;
   the at least two sensor coils being mounted to the generally planar surface of the printed circuit board in a generally co-planar fashion along the generally planar surface, the central axes of the sensor coils being oriented at an obtuse angle with respect to each other, the sensor coils not overlying each other,
   wherein each of the at least two sensor coils extends through the generally planar surface of the printed circuit board, each of the at least two sensor coils having a portion embedded in the printed circuit board and a portion that extends out of the printed circuit board.

2. The orthopaedic device of claim 1 wherein the at least two coils of the sensor form an angle $\theta$ with respect to each other ranging from about 140 degrees to about 170 degrees.

3. The orthopaedic device of claim 1 wherein the printed circuit board further comprises a plurality of conductive traces and solder joints.

4. The orthopaedic device of claim 1 wherein the orthopaedic device is an intramedullary nail and the sensor is disposed in a distal portion of the intramedullary nail.

5. The orthopaedic device of claim 1, further comprising an elongated body having an outer surface with at least one structure for accommodating the inductive electromagnetic sensor.

6. The orthopaedic device of claim 1, wherein the orthopaedic device is a probe configured for removable engagement with an orthopaedic stabilizing structure.

7. The orthopaedic device of claim 1, wherein the mounting platform has a length that is greater than the width of the mounting platform, wherein the generally planar surface is a generally rectangular surface that extends in a plane parallel to the length and the width.

8. A system for identifying a landmark, the system comprising:
   a field generator for generating a magnetic field;
   an orthopaedic device located within the magnetic field, the orthopaedic device having at least one landmark;
   at least one sensor comprising:
      a non-cylindrical mounting platform comprising a printed circuit board comprising a polyamide polymer, the printed circuit board having a generally planar surface and an aspect ratio of greater than about 1.5:1, the mounting platform having a height and a width, the height being smaller than the width, wherein the height ranges from about 0.2 mm to about 1 mm, and the width is less than about 3 mm; and
      at least two sensor coils mounted to the generally planar surface of the printed circuit board, each of the at least two sensor coils defining a central axis, the at least two sensor coils configured to provide data indicating a position in six degrees of freedom in response to receiving electromagnetic fields,
   the at least two sensor coils being mounted to the generally planar surface of the printed circuit board in a generally co-planar fashion along the generally planar surface, the central axes of the sensor coils being oriented at an obtuse angle with respect to each other, the sensor coils not overlying each other, the at least one sensor being spaced apart from the at least one landmark by a set distance,
wherein each of the at least two sensor coils extends through the generally planar surface of the printed circuit board, each of the at least two sensor coils having a portion embedded in the printed circuit board and a portion that extends out of the printed circuit board;
a landmark identifier; and
a processor for processing sensor data from the at least one sensor and using the set distance to determine the position of the landmark identifier relative to the at least one landmark.

9. The system of claim 8 wherein the at least two coils of the sensor form an angle θ with respect to each other ranging from about 140 degrees to about 170 degrees.

10. The system of claim 8, wherein the mounting platform has a length that is greater than the width of the mounting platform, wherein the generally planar surface is a generally rectangular surface that extends in a plane parallel to the length and the width.

11. A method for identifying a landmark, the method comprising:
providing an orthopaedic device and a first sensor disposed at a known location relative to the orthopaedic device, the orthopaedic device having a proximal end portion, a distal end portion and at least one landmark disposed on the distal end portion, the first sensor comprising (i) a non-cylindrical mounting platform comprising a printed circuit board comprising a polyamide polymer, the printed circuit board having a generally planar surface and an aspect ratio of greater than about 1.5:1, the mounting platform having a height and a width, the height being smaller than the width, wherein the height ranges from about 0.2 mm to about 1 mm, and the width is less than about 3 mm; and (ii) at least two sensor coils mounted to the generally planar surface of the printed circuit board, each of the at least two sensor coils defining a central axis, the at least two sensor coils configured to provide data indicating a position in six degrees of freedom in response to receiving electromagnetic fields, the at least two sensor coils being mounted to the generally planar surface of the printed circuit board in a generally co-planar fashion along the generally planar surface, the central axes of the sensor coils being oriented at an obtuse angle with respect to each other, the sensor coils not overlying each other, wherein each of the at least two sensor coils extends through the generally planar surface of the printed circuit board, each of the at least two sensor coils having a portion embedded in the printed circuit board and a portion that extends out of the printed circuit board;
attaching the orthopaedic device to one or more bones of a patient;
targeting the at least one landmark using a landmark identifier and an output of the first sensor; and
engaging at least one of a tool and a fastener with the at least one landmark using the landmark identifier.

12. An orthopaedic device comprising:
an inductive electromagnetic sensor comprising:
a non-cylindrical mounting platform comprising a printed circuit board comprising a polyamide polymer, the printed circuit board having a generally planar surface and an aspect ratio of greater than about 1.5:1; and
at least two sensor coils mounted to the generally planar surface of the printed circuit board, each of the at least two sensor coils defining a central axis, the at least two sensor coils configured to provide data indicating a position in six degrees of freedom in response to receiving electromagnetic fields;
the at least two sensor coils being mounted to the generally planar surface of the printed circuit board in a generally co-planar fashion along the generally planar surface, the central axes of the sensor coils being oriented at an obtuse angle with respect to each other, the sensor coils not overlying each other,
wherein each of the at least two sensor coils extends through the generally planar surface of the printed circuit board, each of the at least two sensor coils having a portion embedded in the printed circuit board and a portion that extends out of the printed circuit board, and wherein the at least two coils of the sensor form an angle θ with respect to each other ranging from about 140 degrees to about 170 degrees.

* * * * *